United States Patent

Birngruber et al.

Patent Number: 6,095,648
Date of Patent: Aug. 1, 2000

[54] PROCESS AND ARRANGEMENT FOR EXAMINING A SECTION OF THE EYE

[75] Inventors: Reginald Birngruber, Lübeck; Christian Scholz, Norderstedt; Peter Koch; Ralf Engelhardt, both of Lübeck, all of Germany

[73] Assignee: Herbert Schwind GmbH & Co. KG, Kleinostheim, Germany

[21] Appl. No.: 09/263,844

[22] Filed: Mar. 8, 1999

[30] Foreign Application Priority Data

Mar. 9, 1998 [DE] Germany ............ 198 10 136
Mar. 20, 1998 [DE] Germany ............ 198 12 297

[51] Int. Cl.$^7$ ....................................... A61B 3/10
[52] U.S. Cl. ............................. 351/214; 351/216
[58] Field of Search ........................... 351/205, 206, 351/211, 214, 216, 219, 221, 246, 247

[56] References Cited

U.S. PATENT DOCUMENTS

| | | |
|---|---|---|
| 5,071,421 | 12/1991 | Stahl . |
| 5,320,113 | 6/1994 | Tan . |
| 5,321,501 | 6/1994 | Swanson et al. . |
| 5,374,272 | 12/1994 | Arpa et al. . |
| 5,493,109 | 2/1996 | Wei et al. . |
| 5,506,634 | 4/1996 | Wei et al. . |
| 5,537,162 | 7/1996 | Hellmuth et al. . |
| 5,706,073 | 1/1998 | Volk ........................ 351/212 |

FOREIGN PATENT DOCUMENTS

| | | |
|---|---|---|
| 0630611 | 12/1994 | European Pat. Off. . |
| 6-205741 | 7/1994 | Japan . |
| 92/19930 | 11/1992 | WIPO . |
| 93/14702 | 8/1993 | WIPO . |

*Primary Examiner*—George Manuel
*Attorney, Agent, or Firm*—Evenson, McKeown, Edwards & Lenahan, P.L.L.C.

[57] ABSTRACT

Systems, methods, and apparatus are provided for deriving the relative position of an eye by tracking a boundary of the eye such as the limbus (i.e., the interface between the white sclera and the colored iris). A technique for tracking the position of the eye of patient comprises directing light to an annular region of the eye between the sclera and the iris and receiving reflected light from that region. The intensity of the reflected light is then measured to determine a relative position of the eye. In some embodiments, the measured region is scanned around the boundary. In other embodiments, a light spot is scanned around a substantially annular trajectory radially outward from the pupil. The signals corresponding to the intensity of the reflected light are then processed and measured to determine the eye's position. A flap of tissue covering the boundary may be automatically detected so as to selectively measure the boundary away from the flap. The invention also provides for integrating the eye tracker into a laser eye surgery system.

13 Claims, 1 Drawing Sheet

PROCESS AND ARRANGEMENT FOR EXAMINING A SECTION OF THE EYE

BACKGROUND OF THE INVENTION

The present invention relates to a process for examining a section of the eye by exposing the section to light by way of a point light source and measuring the backscattered light. The light from the point light source is imaged in a plane, deflected, and directed for scanning the eye section to be examined. The light reflected on the eye section to be examined is sensed and evaluated by optical coherence tomography (OCT technique). The invention further relates to an arrangement for examining a section of the eye having a point light source, an optical imaging device for imaging the point light source in a plane, a scanning device for producing scanning movement of the point light source, and an optical coherence tomography device for evaluating the light reflected by the section of the eye to be examined.

One process and one arrangement of this type are known from U.S. Pat. No. 5,493,109.

For examining the eye, different photography techniques have been used for the anterior and posterior eye sections. In the field of ophthalmology, a fundus camera or a slit lamp has been used, together with an ophthalmoscopy lens such as a contact lens or a Volk lens, for displaying the posterior eye section. The anterior eye section can be displayed by using a slit lamp. Examination of the posterior eye section on the basis of optical coherence tomography (OCT) by way of a fundus camera is known. Corresponding equipment is described, for example, in International Patent Document WO 92/19930 and U.S. Pat. Nos. 5,537,162, 5,506,634, 5,493,109 and 5,321,501. The known equipment is optimized with respect to examination of the posterior section (fundus) of the eye.

An ophthalmologic instrument is known from Japanese Patent Document JP 6-205,741 A, in which a slit lamp is provided as an illuminating system and a measuring device is provided. The measuring device comprises a laser light source, a scanning mirror, a beam splitter, and a photo-electric converter element as well as a light emitter and a filter. The light source emits a directional laser beam for a therapeutic laser light source. Positioning of the directional laser beam is monitored by the photo-electric converter element and the light-emitting element by way of a microscope. When the directional laser has reached a desired position, the therapeutic laser is switched on and the light of this laser is coupled by way of a mirror into the directional laser beam path.

In order to avoid inhomogeneities, particularly of the refracting media, during the OCT of the posterior eye section, a complicated and lengthy adjusting operation is required in order to direct the OCT beam path past the inhomogeneities of the eye to the posterior eye section. When the OCT-technique is used, the adjustment and the targeting operation by which the OCT beam path (sample beam) is directed at the fundus of the eye, particularly at the retina, requires special training and instructions as well as constant practice by the examining physician.

In an arrangement known from FIG. 1 of U.S. Pat. No. 5,537,162, the sample beam path of the OCT interferometer is focussed in the focal plane of a slit lamp microscope. By way of an ophthalmoscopy lens constructed as a Volk lens, in conjunction with the refracting media of the eye, the focal plane of the slip lamp microscope is imaged onto the retina of the eye.

The known arrangement can be used only for OCT-scanning of the posterior eye section. In this case, two separate deviation mirrors are used for producing the sectional views of the eye with an arbitrary alignment. The separate deviation mirrors, however, cause a beam offset and, if the coating is not optimal, produce a double image of the eye. In addition, the working distance between the instrument and the patient's eye is reduced because both deviation mirrors are situated in front of the last optical constructional element of the slit lamp. The use of necessary optical devices, such as an ophthalmoscopy lens, becomes more difficult as a result.

SUMMARY OF THE INVENTION

It is therefore an object of the invention to provide a process and an arrangement of the initially mentioned types which considerably simplify the adjusting and targeting operation for the examination of the concerned eye section using the OCT technique.

According to the invention, this object is achieved by imaging the point light source together with the slit of a slit lamp in conjugated planes and subsequently superimposing the imaged point light source and slit into a joint image or jointly imaging them in a plane. Joint imaging of the slit and the point light source is directed by a slit imaging lens system to the eye section to be examined and is guided during scanning. The reflected light is returned by the same beam path to the point light source for coherence tomography. An arrangement for performing these operations includes a coupling-in lens system which combines imaging of the point light source and a slit of a slit lamp by way of a slit imagining lens system into a joint image plane and images them jointly on the eye section to be examined. The scanning device is constructed such that the imaged point light source is moved during the scanning operation in the longitudinal direction of the imaged slit or in a direction defined relative to the imaged slit. The reflected light is returned by the same beam path to the point light source. Advantageous further developments of the invention are also claimed.

The invention combines conventional examination of a selected eye section by way of slit illumination (an optical sectional image process) with an OCT technique (a coherent sectional image process) which obtains a sectional image of the examined eye section which is preferably produced by coherent light. In this case, posterior sections (cornea, iris, lens) as well as posterior sections (vitreous body, retina, choroid) of the eye can be examined and detected by the same diagnostic instrument using the OCT technique.

The invention uses instruments established in the field of ophthalmology (slit lamp, ophthalmoscopy lens) for adjusting and targeting the OCT-sample beam scanning the examination site on is the eye section. In this case, a part of the slit lamp lens system is advantageously used for guiding the OCT-sample beam path.

Examination using a slit lamp by an ophthalmologist is routine. As a result, the adjusting and targeting operation, which is considerably more complicated and requires higher expenditures when the conventional OCT diagnostic technique is used, is simplified considerably and is essentially reduced to the adjusting operations required for the conventional slit lamp technique. Furthermore, it is possible to carry out eye examinations by way of the conventional slit lamp technique and by way of the OCT technique using one diagnostic instrument and thereby produce a better and more precise correlation between slit lamp images and OCT sectional images.

Conventional slip lamp manipulations can be advantageously used to successively obtain different sectional images of an examination site on the eye. These sectional images can be taken parallel to one another and side-by-side. However, it is also possible to obtain mutually crossing sectional images of an examination site on the eye.

In the present invention, a punctiform illumination and measuring device (PBME) beams in and measures the light, particularly of an OCT interferometer, and may be constructed, for example, as a fiber end of a sample arm of the OCT interferometer. The PBME is coupled by an imaging lens system with the beam path of slit illumination such that the lens systems and adjusting devices, used in a conventional manner for directing a slit image of a slit lamp to the eye section to be examined, direct the sample beam together with the slit image to the eye section to be examined. When measuring the eye section to be examined, the scanning movement is defined by the alignment of the imaged slit. The scanning movement, in particular, takes place parallel to or along the slit image.

For this purpose, the images of the PBME and of the slit can be superimposed by a coupling-in lens system or a superimposing lens system, which may be constructed, for example, as a dichroitic splitter (mirror). The PBME and the slit can be imaged either in a common plane or in planes conjugated with respect to one another in order to subsequently be directed jointly at the section of the eye to be examined by the lens system.

With respect to the coupling-in lens system or the superimposing lens system, the slit lamp can be arranged such that the common plane, in which the slit is imaged together with the PBME, is situated in front of the superimposing lens system in the OCT beam path coming from the punctiform emission surface of the PBME. It is sufficient for scanning to deflect the OCT sample beam in the common plane (conjugated slit plane) in the direction of the imaged slit. In an alternative embodiment, scanning can take place such that the imaged PBME is moved in an arbitrary curve shape which, however, is fixedly defined relative to the imaged slit. This can take place by using movable swivelling mirrors. Guiding of the OCT sample beam together with the optical structural components assigned to the slit illumination, specifically the slit imaging lens system, takes place behind the superimposing lens system. Alignment of the scanning illumination beam takes place in the anterior eye section (cornea, iris, lens) by way of the lens system pertaining to the slit lamp. For examination of the posterior eye section, imaging of the image produced by the slit imaging lens system of the PBME and the slit takes place by using an ophthalmoscopy lens, such as a Volk lens, and the refracting media of the eye (FIG. 1 of U.S. Pat. No. 5,537,162).

The imaging and guiding lens system situated in the OCT sample beam path in front of the coupling-in lens system or superimposing lens system can be connected with the slit lamp, particularly the slit lamp head having the slit and the slit lo illumination, so that during movement (rotating, swivelling, tilting) of the slit lamp head and the resulting movement of the slit, for example, rotation about the optical axis occurs. Simultaneously, the imaging and guiding lens system, particularly the scanning devices used for scanning along the slit, are rotated along or moved along. As a result, in any slit position, the OCT sample beam is imaged in the common plane. In the same manner, the slit imaging lens system can also be moved along. Advantageously, the lens system, such as the OCT interferometer, required only for the OCT can be situated away from the examination site so that, during examination of the patient, there will be no hindrance at the examination site.

When a Volk lens is used with the slit lamp, the focal length of the image essentially depends on the distance of the Volk lens from the slit lamp. When this distance is correctly coordinated, imaging is also maintained when the distance between the measuring arrangement and the patient is changed, because the beam path is parallel between the Volk lens and the right-sighted eye of the patient. The OCT measuring process is sensitive with respect to this distance and the distance has to be variable. Another development of the invention varies this distance when the adjustment of the focal position has been found and thus the optical path in the sample beam path is varied without changing the focal position.

As a further development of the invention, for imaging an intermediate image containing the slit and the PBNE onto the fundus of the eye, for example, the retina of the eye, the Volk lens can be fixed at a certain distance from this intermediate image. This is permitted by a connection of the Volk lens with the slit lamp, particularly the slit lamp head, so that the distance of the Volk lens from the intermediate image can be fixedly adjusted for examination on the eye. A holding device is used for this purpose, and the Volk lens is held movably in all degrees of freedom while maintaining a certain distance from the slit. Advantageously, a cardanic mounting of the Volk lens in the holding device is used.

The holding device may be formed of vertical and horizontal rods which are connected with one another in an articulated manner.

BRIEF DESCRIPTION OF THE DRAWINGS

The invention will be explained in detail by referring to the drawing figures.

DESCRIPTION OF THE PREFERRED EMBODIMENTS

Figure 1:
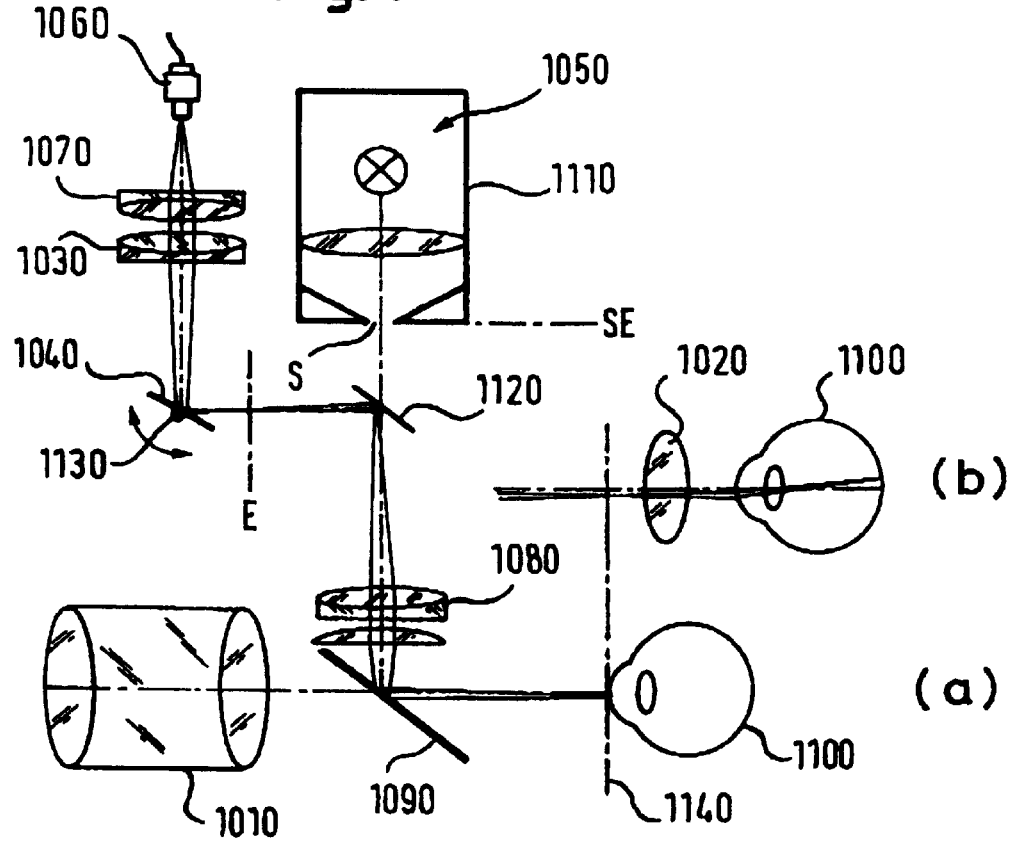
FIG. 1 is a schematic view of one embodiment of the invention.

The embodiment illustrated schematically in FIG. 1 shows an arrangement for examining the anterior and posterior sections of an eye 1100. For this purpose, a punctiform illumination measuring device (PBME) 1060 emits coherent light such as a laser beam. The PBME 1060 may be constructed as the fiber end of a light-guiding fiber of an optical coherence tomography interferometer (OCT interferometer). The light emerging from the fiber end or the PBME 1060 is collimated by a collimator lens system 1070. The light is then focussed by a focussing lens system 1030 in a plane E or imaged by an imaging lens system in the plane E. A scanning device 1040 is situated between the plane E and the imaging system consisting of the focussing lens system 1030 and the collimator lens system 1070. The scanning device is constructed as a swivellable mirror in the illustrated embodiment. The mirror can be driven, for example, by a galvanometer to generate the scanning movement and can be disposed in a swivel bearing 1130.

A coupling-in lens system or a superimposing lens system 1120, which may be constructed as a dichroitic mirror, superimposes the laser beam with the illumination beam path of a slit lamp.

The slit lamp includes a slit lamp head 1110 which has a slit S in a slit plane SE. The slit S is illuminated by an illuminating system 1050. The superimposing lens system 1120 (dichroitic mirror) brings the plane E into a plane which is conjugated with respect to the slit plane SE. In this manner, the PBME 1060, which may be the fiber end of a sample arm of the OCT interferometer, is guided together with the slit S or with the slit plane SE of the slip lamp.

A slit imaging lens system 1080 follows the superimposing lens system 1120 and is part of the slit illumination lens system. By way of a deflection lens system 1090 which may be constructed as a deflection mirror, the slit imaging lens system images the conjugated planes E and SE into the section of the eye 1100 to be examined in an image plane 1140. In the lower portion (a) of FIG. 1, the plane 1140 is situated in the anterior eye section.

As illustrated in the portion (b) of FIG. 1, examinations on the posterior eye section (for example, the retina) can be made by an ophthalmoscopy lens. The ophthalmoscopy lens is constructed, for example, as a Volk lens 1020 and is arranged between the patient's eye 1100 and the image plane 1140. By way of the refracting media of the eye, another imaging of the image plane 1140 takes place onto the posterior eye section.

The slit lamp head 1110 and the swivel bearing 1130 for the scanning device 1040 as well as the imaging lens system (focussing lens system 1030, collimator lens system 1070) for the PBME 1060 can be rigidly connected with one another. In addition, the slit imaging lens system 1090 and the superimposing lens system 1120 can be rigidly connected with the slit lamp head 1110. During movement (rotating, tilting, swivelling) of the slit lamp head 1110 and the resulting movement of the slit S, the scanning device 1040 is moved along simultaneously. In addition, the assigned lens systems 1030, 1070 and 1080 are moved along so that guiding-together of the PBME 1060 with the slit S of the slit lamp by the superimposing lens system 1120 is ensured for any slit position. In this manner, only by operating the slit lamp, an alignment of the OCT beam path for scanning the eye section to be examined is achieved and the beam is directed to the examination site on the eye.

During scanning, the light beam coming from the PBME is guided through the slit imaging lens system 1080 and the deflecting device 1090 to the examination site on the eye section. Scanning of the examination site takes place along the imaged slit. Scanning movement takes place by way of the scanning device 1040 constructed, for example, as a swivelling mirror. The reflected measuring beam is guided by way of the above-explained structural optical units back to the PBME. By way of the evaluation of the measuring beam, a sectional image of the examination or measuring site is generated. The combination of the slit lamp technique and the scanning technique therefore results in the production of an optical sectional image. Multiple scanning successively produces several sectional views which, for example, are situated parallel and side-by-side is or in a crossed manner with respect to one another.

In another embodiment, arbitrary patterns with a defined position relative to the slit image can be scanned, for example, by integration of at least one additional swivelling mirror.

Figure 2:
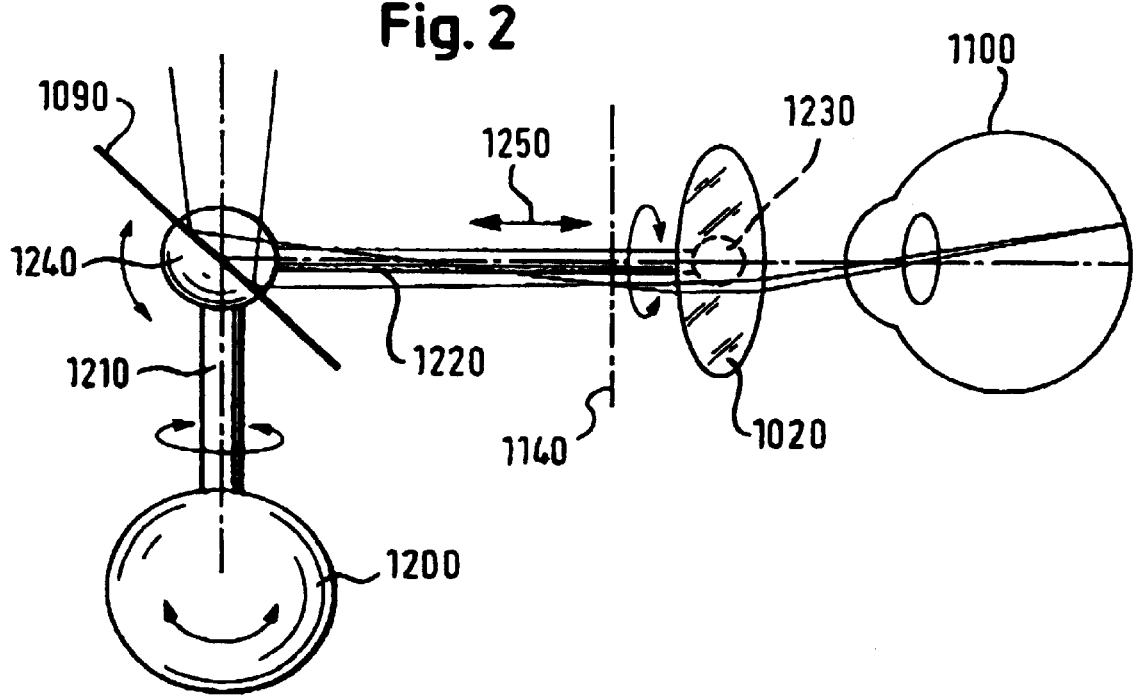
FIG. 2 is a view of an embodiment according to a further development of the invention.

FIG. 2 is a schematic view of an embodiment of a holding arrangement by which the Volk lens 1020 can be held with respect to the image plane 1140 of the slit lamp at a fixed distance which can be adjusted for respective examination. The holding device is formed by a horizontal rod 1220 at which, particularly at the end, the Volk lens 1020 is movable in all degrees of freedom about a pivot disposed in a cardan joint 1230. As a result, movement of the Volk lens into any position can take place for optimal adjustment of the exposure operation with the scanning laser beam of the OCT measuring device. The horizontal rod 1220 is connected by a joint 1240, in the form of a hinge, with a vertical rod 1210. The joint 1240 is situated at the intersection point of the deflecting lens system 1090. By way of the joint 1240, the centering of the Volk lens 1020 can be continuously adjusted. The vertical rod 1210 is rotatably fixed on the slit lamp by a holder 1200 which may be constructed as a magnetic holder. This maintains an adjusted distance of the Volk lens 1020 with respect to the image plane 1140 of the slit lamp.

The axial distance of the Volk lens 1020 with respect to the image plane 1040 can be roughly preadjusted by rotating the whole holder 1200. A precise adjustment of the axial distance, as well as an adaptation of the focal position when, for example, the patient has defective vision, can be ensured by a longitudinal adjustment (in the direction of the double arrow 1250) of the horizontal rod 1220.

When the proper adjustment of the focal position is found, it is therefore possible to vary the optical path without any change of the focal position between the Volk lens 1020 and the section of the patient's eye 1100 to be examined.

The holding arrangement for the Volk lens described allows the physician to observe and control other events during an examination. The magnetic adaptation of the holding arrangement makes a fast change, which presents no problems, possible between the right and the left eye. This is because, as required, the magnetic holder can be mounted on one of the two sides of the slit lamp. The firm connection of the Volk lens 1020 with the slit lamp, particularly the slit lamp head 1110, allows the distance between the Volk lens 1020 and the image plane 1040 to remain unchanged during movement of the slit lamp.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Process for examining an eye section of an eye by exposing the section to light with a point light source and measuring backscattered light, the point light source being imaged in a plane, deflected, and directed for scanning the eye section to be examined, the light reflected on the eye section to be examined being sensed and being evaluated by coherence tomography, comprising the steps of:

imaging the point light source together with a slit of a slit lamp in conjugated planes and subsequently superimposing the imaged light source and slit of the slit lamp into a joint image or jointly imaging them in a plane, directing joint imaging of the slit and the point light source by way of a slit imaging lens system to the eye section to be examined which is guided during scanning, and returning reflected light by way of the same beam path to the point light source for the coherence tomography.

2. Process according to claim 1, wherein several different scanning operations are carried out successively on the eye section to be examined.

3. Arrangement for examining an eye section of the eye comprising:

a point light source, an optical imaging device which images the point light source in a plane, a scanning device which generates a scanning movement of the point light source, an optical coherence tomography device which evaluates light reflected by the eye section to be examined, and a coupling-in lens system which combines imaging of the point light source and a slit of a slit lamp by way of a slit imagining lens system into a joint image plane and images them jointly on the eye section to be examined, wherein the scanning device is constructed such that the imaged point light source is moved during a scanning operation in a longitudinal direction of the imaged slit or in a direction defined relative to the imaged slit, and wherein the reflected light is returned by the same beam path to the point light source.

4. Arrangement according to claim 3, wherein the slit imaging lens system is arranged, in the direction of the eye to be examined, following the superimposing lens system.

5. Arrangement according to claim 4, wherein the joint image plane, in which the slit plane and the point light source are combined, is situated, in the direction of the eye to be examined, in front of the superimposing lens system.

6. Arrangement according to claim 5, wherein movement of imaging and guiding devices imaging the point light source into the joint image plane is coupled with movement of the slit and the slit imaging lens system.

7. Arrangement according to claim 4, wherein movement of imaging and guiding devices imaging the point light source into the joint image plane is coupled with movement of the slit and the slit imaging lens system.

8. Arrangement according to claim 3, wherein the joint image plane, in which the slit plane and the point light source are combined, is situated, in the direction of the eye to be examined, in front of the superimposing lens system.

9. Arrangement according to claim 3, wherein movement of imaging and guiding devices imaging the point light source into the joint image plane is coupled with movement of the slit and the slit imaging lens system.

10. Arrangement for examining an eye section of the eye comprising:

a point light source, an optical imaging device which images the point light source in a plane, a scanning device which generates a scanning movement of a light beam directed at eye section, a detector device for detecting light reflected by the eye section to be examined, and a Volk lens, arranged between the eye to be examined and an intermediate image containing a slit and the point light source, which images the intermediate image onto the fundus of the eye, the Volk lens being arranged at a defined distance with respect to an intermediate image plane.

11. Arrangement according to claim 10, and further comprising a holding arrangement by which the Volk lens can be fastened at a defined distance from the intermediate image plane.

12. Arrangement according to claim 11, and further comprising a cardanic mounting in which the Volk lens is disposed in the holding arrangement.

13. Arrangement according to claim 11, and further comprising a cardanic mounting in which the Volk lens is disposed in the holding arrangement.

* * * * *